US00PP12863P2

(12) United States Plant Patent
Crooke

(10) Patent No.: US PP12,863 P2
(45) Date of Patent: Aug. 20, 2002

(54) MACINTOSH APPLE VARIETY NAMED 'MIRIELA'

(75) Inventor: Richard K. Crooke, Ashford, CT (US)

(73) Assignee: Michael L. Janket, Putnam, CT (US)

( * ) Notice: Subject to any disclaimer, the term of this patent is extended or adjusted under 35 U.S.C. 154(b) by 0 days.

(21) Appl. No.: 09/684,042

(22) Filed: Oct. 6, 2000

(51) Int. Cl.[7] ..... A01H 5/00

(52) U.S. Cl. ..... Plt./165

(58) Field of Search ..... Plt./165

*Primary Examiner*—Bruce R. Campell
*Assistant Examiner*—Susan B. McCormick
(74) *Attorney, Agent, or Firm*—Klarquist Sparkman LLP

(57) ABSTRACT

The 'Miriela' variety of MacIntosh apple tree is characterized by a later fruit maturity date, harder texture, slower ripening/softening rate, lower flesh ethylene level, and strong resistance to pre-harvest drop.

5 Drawing Sheets

The present invention relates to a new and distinct variety of MacIntosh apple tree named 'Miriela,' which was discovered by Richard K. Crooke in a cultivated area of an existing orchard located at 317 Bebbington Road, Ashford, Conn., 06278. This new variety was discovered as a full-sized tree of unknown parentage grafted onto 'Malling #7' rootstock (unpatented).

The 'Miriela' variety differs from other MacIntosh strains known to the inventor in that the 'Miriela' variety matures approximately 4 weeks later, has a harder texture, ripens/softens at a slower rate, has a lower flesh ethylene level and a strong resistance to pre-harvest drop.

Asexual reproduction of this new variety by budgrafting and cleft/bark grafting, as performed under the direction of Richard K. Crooke, shows that the foregoing and all other characteristics and distinctions come true to form and are established and transmitted through succeeding propagations. Moreover, the new apple variety exhibits good union between the root-stock and the grafting stock with no rejection tendencies observed to date.

The accompanying Figures show typical specimens of the new tree, leaves, and fruit of this new variety, depicted in color as nearly true as it is reasonably possible to make the same in a color illustration of this character.

The following is a detailed description of the invention based on the original tree which was planted in 1982, and observed in fruiting stage since 1992 in an existing orchard in Ashford, Conn. Color descriptions and other terminology are used herein in accordance with ordinary dictionary significance unless otherwise noted with reference to The Royal Horticultural Society Colour Chart (R.H.S.). It should be noted that growth and/or color varies with time of year, lighting conditions, and soil and nutrient conditions. For example, leaf colors may be brighter green if the trees are grown in soil with greater nitrogen concentrations, and may be more yellow when grown in soil containing lesser amounts of nitrogen.

DETAILED DESCRIPTION

Figure 1:
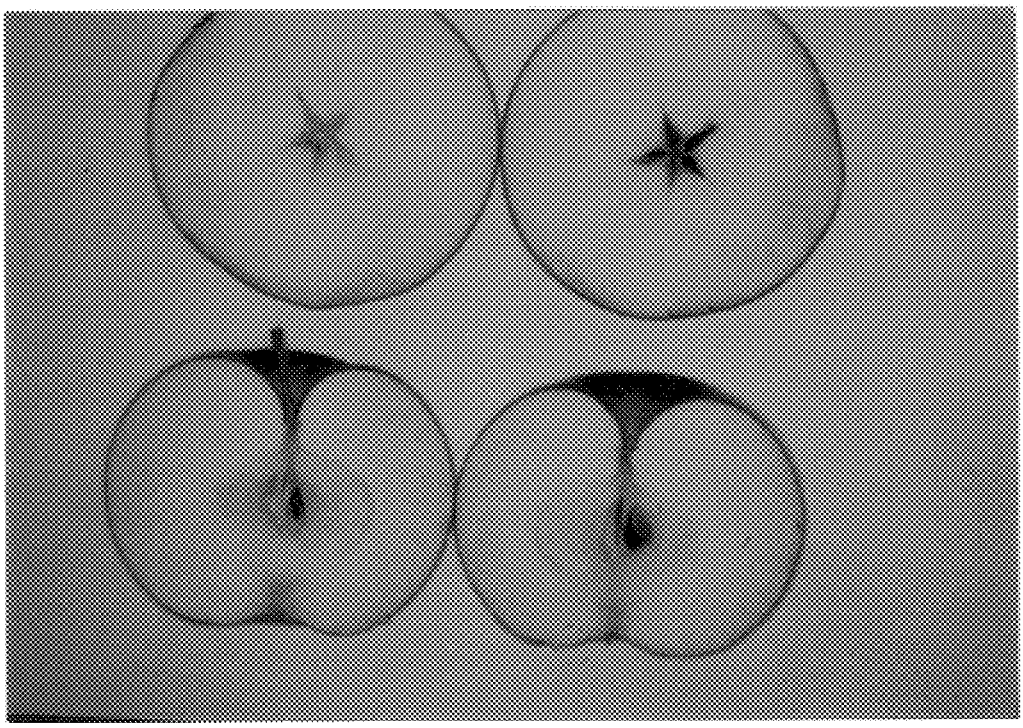
FIG. 1 shows cross-sectional views of representative fruits from the apple variety 'Miriela'.
Figure 2:
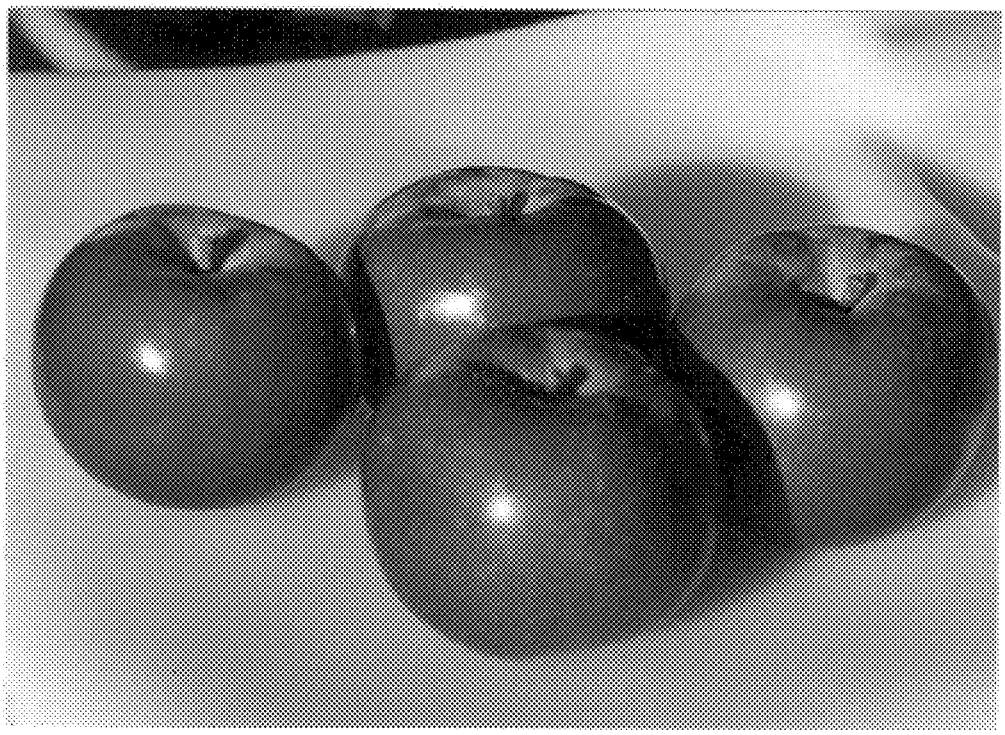
FIG. 2 shows representative whole fruits from the 'Miriela' variety.
Figure 3:
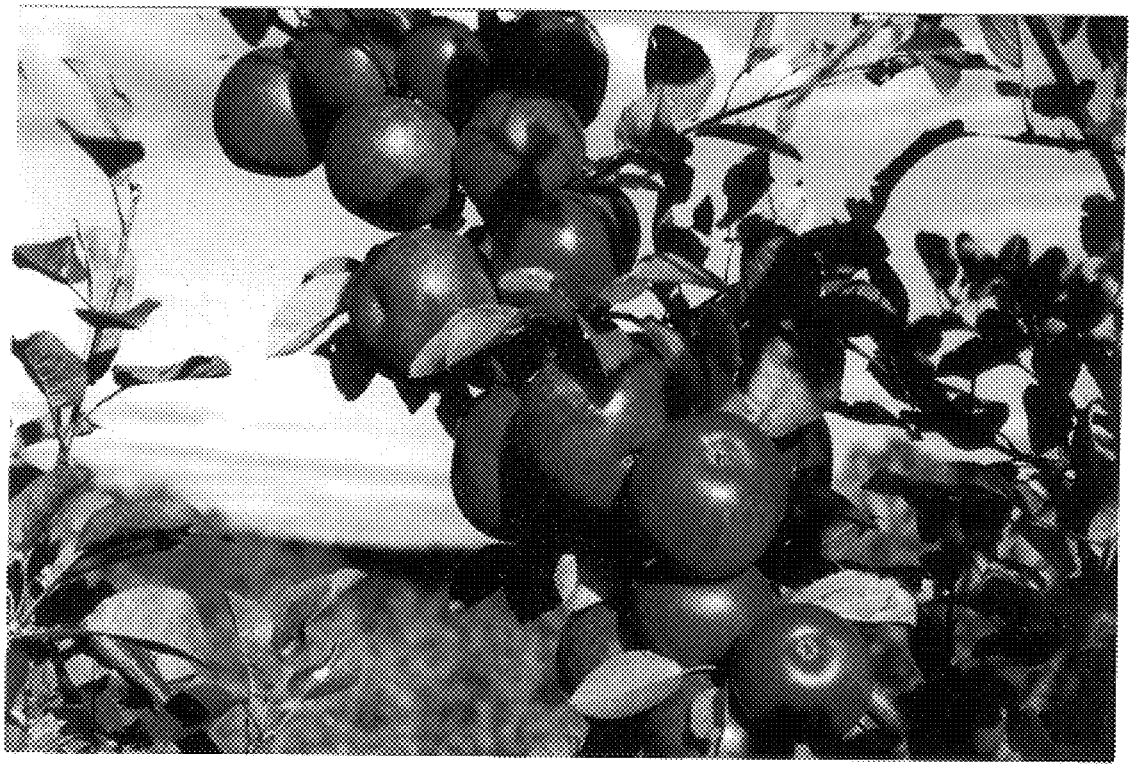
FIG. 3 shows a representative limb of the 'Miriela' variety with several fruits.
Figure 4:
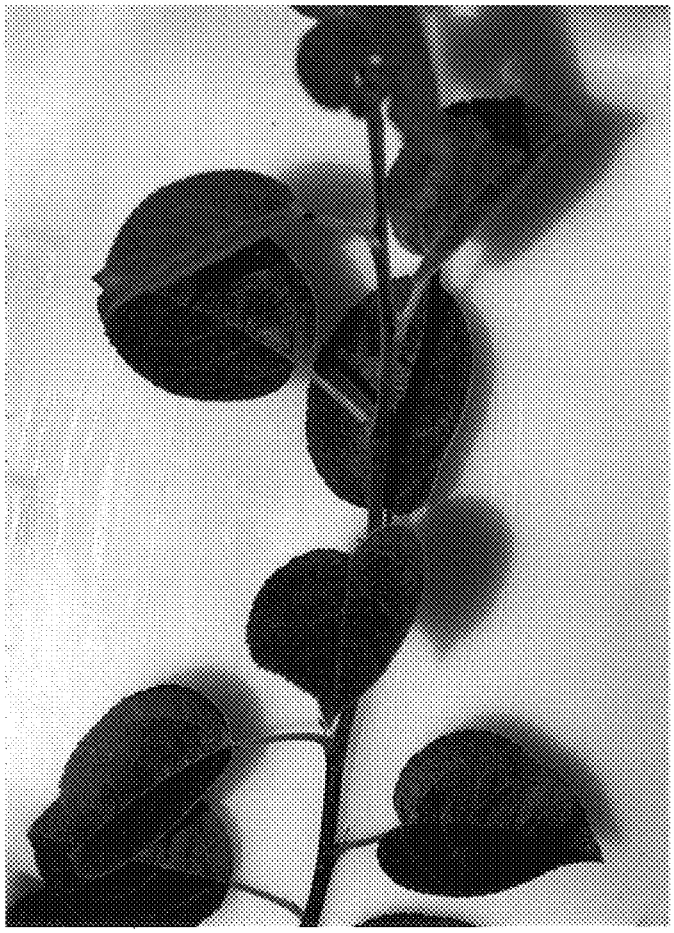
FIG. 4 shows a branch from the 'Miriela' variety with several representative leaves.
Figure 5:
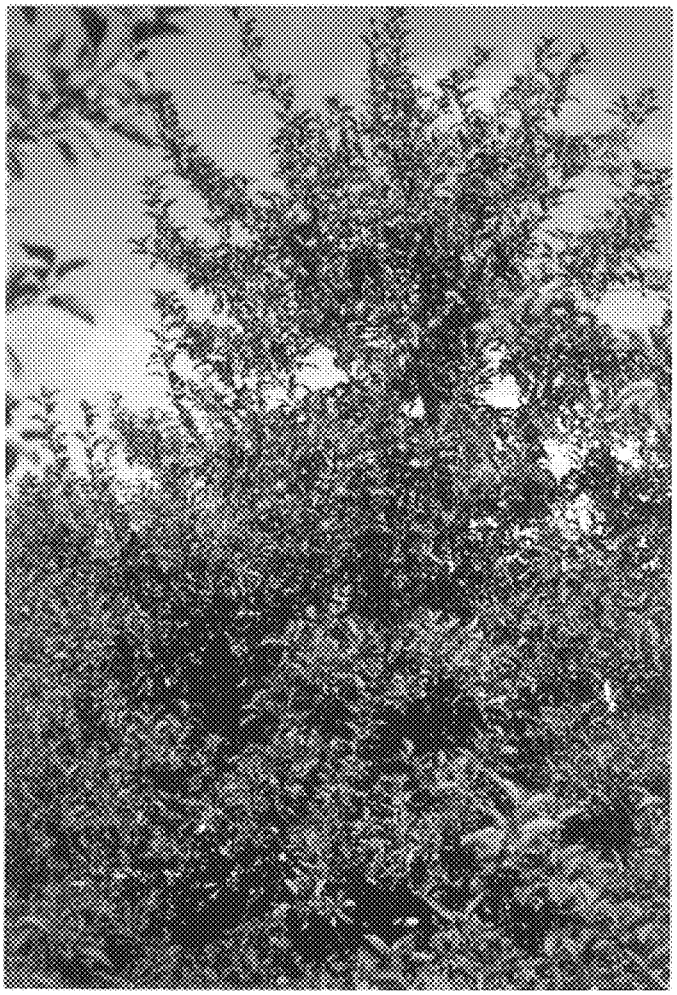
FIG. 5 shows a tree of the 'Miriela' variety.

The following is a detailed description of the new 'Miriela' variety based upon observations of the original tree:

Date of picking:

*First picking date.*—Nov. 4, 1994 (Original tree).

*Subsequent picking dates.*—Oct. 22, 1996; Oct. 21, 1997; Oct. 24, 1998; and Oct. 23, 1999.

*Average picking dates.*—Between October 17 and November 8. Harvest years 1994–1999, Ashford, Conn.

*Picked for starch characteristics.*—Starch iodine test shows starch levels of 3 and higher.

Botanical Description

Botanical classification: *Malus pumila* Mill.

Tree:

*Medium size.*—The observed tree, growing in Ashford, Conn., grown on 'Malling #7' rootstock (unpatented) and aged 19 years, measured 17 feet high with a canopy spreading 14 feet in diameter.

*Vigor.*—Medium. Comparable to other Macintosh strains.

*Habit.*—Upright and spreading.

Trunk: Medium thickness. Proportional to overall tree vigor. Measures 8" at a height of 12" above ground, which is typical for McIntosh varieties.

*Trunk bark texture.*—Smooth up to 12–14 years, then typical exfoliation occurs.

*Trunk bark color.*—At 18 years of age bark color was like RHS 199B.

Branches: Upright and spreading. Thinner than standard MacIntosh strains by 25%.

*Branch angle at emergence.*—Nearly horizontal to slightly upright (approximately 20° above horizontal axis).

*Branch color.*—Color of one year dominant branch is like RHS 200B. Color tends to get lighter with age (like RHS 199A).

*Branch pubescence.*—Heavy pubescence on same year shoots.

*Branch lenticels.*—Shape: Round. Quantity: Numerous. Color: like RHS 165C. Size: <1.0 mm diameter.

Internodes: Average length on 1 year old shoot: 1⅝".

Bearing: Annual and heavy. Similar to standard strains of MacIntosh.

Hardiness: Winter injury unnoticed. Tree appears to be as hardy as standard MacIntosh strains.

Disease and insect resistance/susceptibility: Susceptible to apple scab. Virtually the same resistance and susceptibility as standard MacIntosh strains.

Foliage: Similar to standard types. Fifty typical leaves from a tree grown in Ashford, Conn., were observed to obtain the following average characteristics:

Leaves:

*Size.*—Medium sized. Medium length.

*Overall shape.*—Oval and ovate.

*Length.*—3¼".

*Width.*—2⅛"–2¼".

*Petiole.*—Average: 1¼" Range: 1⅛"–1½".

*Margin.*—Coarsely serrate.

*Tip.*—Abruptly pointed.

*Stipules.*—Non-clasping, 3/16" long.

*Leaf color.*—Upper like RHS 147A. Under like RHS 147C. Petiole like RHS 147C.

*Pubescence.*—Lower heavy, color like RHS 147D.

Flowers: Same structure as the 'Cortland' and 'Macoun' varieties.

*Time of bloom.*—First bloom averages May 4. Petal fall 3–10 days later (weather depending).

*Size of bloom.*—5 petals. 1¼"–1½" diameter.

*Flower color.*—Pale pink like RHS 58C fading to white like RHS 57C, whiter than RHS 155D.

*Petal shape and texture.*—Smooth margins, round apex tapering to a narrow base approximately one-quarter the width of the petals at their widest point, providing an overall obovate shape. Soft, flexible texture.

*Stamen.*—In two obscure whorls; median. Fifteen to twenty stamens present.

*Pistil.*—One pistil. Styles present, united, and pubescent. Glabrous toward apex at branch point.

*Sepals.*—Small, closed or partly open. Lobes short to long, narrow, and acute. Generally 5 in number, measuring 4.5 mm long, tapering to a 3 mm wide base. Gray-green in color, like RHS 141C.

*Pollination requirements.*—Compatible with at least 'Cortland,' 'Jonamac,' and 'Delicious' varieties.

*Fragrance.*—Typical of most apple varieties, pronounced.

Fruit: Light odor of typical MacIntosh fragrance. Slower ripening pattern makes for reduced level of volatiles at any given time during mature stage.

*Maturity.*—Full maturity, starch levels at 5–7.

*Color.*—Fruit covered 40%–90% with primary color.

*Soluble solids.*—Approximately 12.9%–15%.

*Malic acid level.*—Approximately 0.75%.

*Fruit form.*—Fruit roundish to somewhat oblate, regular or obscurely angular. Stem: short approximately ⅝", color green like RHS 142A. Bracts: Present, 1 or 2 in number. Calyx: Present and closed. Segments: Persistent. Inner and outer surface pubescent. Stem Cavity (observation from average of 50 typical apples): Symmetrical, about 9/16" deep. Flaring toward apex. Basin Cavity (observation from average of 50 typical apples): Unsymmetrical, rounded, flaring, narrow base undulate, and pubescent. Locules: Roundish to elliptical, narrowing toward base and apex, smooth, and concave.

Skin: Smooth; thin; tough.

*Texture.*—Little tendency toward cracking. Little or no tendency for greasiness. Little tendency for russetting. Thin to light to moderate bloom.

*Lenticels.*—Round, 1/mm diameter. Color white like RHS 155C color.

*General color effect.*—Blush starts at stripe and fills in.

*Ground color.*—Yellow-Green like RHS 149A.

*Overcolor.*—Color red like RHS 46A. Stripe filling in to blush appearance.

Flesh: Fine, crisp, and tender.

*Color.*—White, slightly tinged with Yellow like RHS 155D.

*Texture.*—Smooth and tender.

*Flavor/juiciness.*—Sweet, 12.7 to 14.5; Brix. Juicy; tart-sweet, can be moderately astringent in early maturity.

*Acidity.*—Moderate acidity, approximately 0.75% malic acid.

*Aroma.*—Typical of cultivar, but slower developing due to reduced rate of ripening over longer time period.

*Firmness.*—16 lbs. at harvest.

Core: Calyx tube short, conical, abaxial, and medium size. Cells wide open. Core lines nearly meeting. Carpels round/elliptical, narrowing toward base, smooth, and concave.

Seed: Rather large seeds. Approximately 5/16"×3/16" long, acute/obtuse, Light Medium Brown like RHS 175A. Not more than 3 seeds per cell.

Keeping quality: Very good in controlled atmosphere. Fair in airstorage. Shelf life in excess of one week post storage.

Storage: Common Storage: Up to 4 months. Controlled Atmosphere Storage: Up to 10 months.

Usage: Dessert, sauce, pies, cobblers, cider.

I claim:

1. A new and distinct variety of MacIntosh apple tree named 'Miriela' substantially as illustrated and described, which displays a later fruit maturity date, harder texture, slower ripening/softening rate, lower flesh ethylene level, and strong resistance to pre-harvest drop.

* * * * *

UNITED STATES PATENT AND TRADEMARK OFFICE

CERTIFICATE OF CORRECTION

PATENT NO. : PP 12,863 P2
DATED : August 20, 2002
INVENTOR(S) : Richard K. Crooke It is certified that error appears in the above-identified patent and that said Letters Patent is hereby corrected as shown below:

Title page,
Item [54], Title, change "MACINTOSH APPLE VARIETY NAMED 'MARIELA'" to -- MACINTOSH TREE NAMED 'MARIELA' --

Column 4,
Line 27, change "*Firmness.*—16 lbs. at harvest" to -- *Firmness*: Approximately 15-16 lbs. when harvested around October 24, in Connecticut. --

Signed and Sealed this

Twenty-fourth Day of February, 2004

JON W. DUDAS
*Acting Director of the United States Patent and Trademark Office*